(12) United States Patent
Dairiki et al.

(10) Patent No.: US 9,277,746 B2
(45) Date of Patent: Mar. 8, 2016

(54) LIQUID COMPOSITION, PROCESS FOR PRODUCING THE LIQUID COMPOSITION, AND ECTOPARASITE CONTROLLING AGENT FOR USE IN MAMMALS AND AVIANS

(75) Inventors: Hiroshi Dairiki, Odawara (JP); Rieko Nakamura, Haibara-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 1157 days.

(21) Appl. No.: 12/226,339

(22) PCT Filed: May 2, 2006

(86) PCT No.: PCT/JP2006/309167
§ 371 (c)(1),
(2), (4) Date: Oct. 14, 2008

(87) PCT Pub. No.: WO2007/129395
PCT Pub. Date: Nov. 15, 2007

(65) Prior Publication Data
US 2009/0069386 A1    Mar. 12, 2009

(51) Int. Cl.
*A61K 31/4439* (2006.01)
*A61K 31/44* (2006.01)
*A61P 33/00* (2006.01)
*A61K 31/426* (2006.01)
*A01N 25/02* (2006.01)

(52) U.S. Cl.
CPC ...................... *A01N 25/02* (2013.01)

(58) Field of Classification Search
CPC ............................... A01N 25/02; A01N 51/00
See application file for complete search history.

(56) References Cited

U.S. PATENT DOCUMENTS

| | | | |
|---|---|---|---|
| 4,915,943 A | 4/1990 | Gago et al. | |
| 6,001,384 A * | 12/1999 | Jeannin | 424/405 |
| 6,300,348 B1 | 10/2001 | Sirinyan et al. | |
| 6,369,054 B1 | 4/2002 | Sirinyan et al. | |
| 2003/0162773 A1 | 8/2003 | Sirinyan et al. | |
| 2006/0046988 A1 * | 3/2006 | Boeckh et al. | 514/248 |
| 2006/0140984 A1 * | 6/2006 | Tamarkin et al. | 424/400 |

FOREIGN PATENT DOCUMENTS

| | | |
|---|---|---|
| EP | 0 669 078 | 8/1995 |
| EP | 0 836 851 | 4/1998 |
| JP | 8-301707 | 11/1996 |
| JP | 9-48938 | 2/1997 |
| JP | 10-53737 | 2/1998 |
| JP | 11-269010 | 10/1999 |
| JP | 2005-154344 | 6/2005 |
| JP | 2006-131751 | 5/2006 |
| JP | 2006-143610 | 6/2006 |
| JP | 2009-522332 | 6/2009 |
| UA | 73920 | 10/2000 |
| UA | 73920 | 12/2000 |
| UA | 73920 | 10/2005 |
| WO | 99/41986 | 8/1999 |
| WO | 99/41987 | 8/1999 |

OTHER PUBLICATIONS

Aug. 30, 2010, Office Action, Korean Patent Application No. 10-2008-7026612 (English-language translation providied).

Japanese Office Action issued for Japanese Patent Application No. 2008-514339, dated Oct. 4, 2011, 8 pages.

European Search Report for 06746017.0, dated Jul. 10, 2012, 7 pages.

* cited by examiner

*Primary Examiner* — Anna Falkowitz
(74) *Attorney, Agent, or Firm* — Kenyon & Kenyon, LLP

(57) ABSTRACT

A liquid composition comprising (a) 21 to 70 parts by weight of a solvent having no nitrogen atom and having a carbonyl or sulfonyl group in the molecule, (b) 30 to 78.9 parts by weight of at least one component selected from the group consisting of a non-cyclic alcohol, an alkylene glycol, a polyalkylene glycol, a triol, a glycol monoacetate and a glycol monoalkyl ether, (c) 0.001 to 30 parts by weight of a physiologically active ingredient, and (d) 0.001 to 49 parts by weight of water.

14 Claims, 2 Drawing Sheets

LIQUID COMPOSITION, PROCESS FOR PRODUCING THE LIQUID COMPOSITION, AND ECTOPARASITE CONTROLLING AGENT FOR USE IN MAMMALS AND AVIANS

TECHNICAL FIELD

The present invention relates to a liquid composition in which a dye is excellent in stability against light and/or heat, to a process for producing the liquid composition, and to an ectoparasite controlling agent for use in mammals and avians.

BACKGROUND ART OF THE INVENTION

As for the formulations of agricultural chemicals (pharmaceutical compositions) or the like, in some cases, dyes are added to the formulations from the viewpoint of easier discrimination of formulations, prevention of misingestion, or the like.

Such dyes are organic colorants, which are generally unstable against light or heat.

For the powdered or particulate formulations, a solid substance in the formulation acts as a covering to protect against the light, and thus there is only a very small possibility of there being a problem in terms of the stability of the dye against light.

However, in the liquid formulations containing no solid, even in the case of using a light-resistant container, or the like, slight penetrated light frequently decomposes the dye in many cases. Further, in a case where a liquid formulation containing a dye is kept at a high temperature over a long period of time, the dye is decomposed by heat in some cases. In addition, in such a case, a liquid composition having an original color tone can not be obtained, and further, a product from the decomposition of the dye causes adverse effects on the efficacy in some cases.

Relating to the present invention, Patent Document 1 describes a formulation containing a: an agonist or antagonist of the nicotinic acetylcholine receptors for insects, b: water, c: non-cyclic alcohols, d: coloring agents, and the like, in predetermined ratios.

However, this document has no description on the selection of a solvent to be used to enhance the stability against light and/or heat of the coloring agent.

Furthermore, Patent Document 2 describes a formulation for percutaneous control of parasitic insects and mites against humans, which has the composition as follows: (i) an agonist or antagonist of the nicotinic acetylcholine receptors of the insects at a concentration of 0.0001 to 20% by weight, based on the total weight of the formulation; (ii) a solvent in a group of cyclic carbonate esters at a concentration of 2.5 to 99.9999% by weight, based on the total weight of the formulation; (iii) in some cases, other solvents in a group of alcohols at a concentration of 0 to 95% by weight, based on the total weight of the formulation, and (iv) in some cases, other auxiliary agents selected from the group consisting of a thickening agent, a spreading agent, a coloring agent, an anti-oxidant, a swelling agent, a preservative, a tackifier, and an emulsifier at a concentration of 0 to 30% by weight, based on the total weight of the formulation.

However, the formulation (composition) as described in this document contains no water. Furthermore, this document has a description indicating that a coloring agent may be contained in the formulation, but has no disclosure on a specific example showing that a coloring agent is added to the formulation.

[PATENT DOCUMENT 1] Japanese Patent Application Publication No. 2002-503682
[PATENT DOCUMENT 2] Japanese Patent Application Publication No. 2000-509023

DISCLOSURE OF THE INVENTION

Problems to be Solved by the Invention

It is an object of the present invention to provide a liquid composition in which a dye is excellent in stability against light and/or heat, a process for producing the liquid composition, and an ectoparasite controlling agent for use in mammals and avians.

Means for Solving the Problems

The inventors of the present invention have studied extensively in order to solve the above-described problems, and as a result, they have found that a dye is stable against light and/or heat in a liquid composition containing (a) a solvent having no nitrogen atom and having a carbonyl or sulfonyl group in the molecule, (b) at least one component selected from the group consisting of a non-cyclic alcohol, an alkylene glycol, a polyalkylene glycol, a triol, a glycol monoacetate and a glycol monoalkyl ether, (c) a physiologically active ingredient, and (d) water at predetermined ratios. In addition, they have found that a composition containing a neonicotinoid-based insecticidally active ingredient as the (c) physiologically active ingredient for the liquid composition is useful for an ectoparasite controlling agent for use in mammals and avians, thereby completing the present invention.

Thus, according to a first aspect of the present invention, the following (1) to (11) liquid compositions are provided.

(1) A liquid composition containing the following components (a) to (d):
(a) 21 to 70 parts by weight of a solvent having no nitrogen atom and having a carbonyl or sulfonyl group in the molecule;
(b) 30 to 78.9 parts by weight of at least one component selected from the group consisting of a non-cyclic alcohol, an alkylene glycol, a polyalkylene glycol, a triol, a glycol monoacetate and a glycol monoalkyl ether;
(c) 0.001 to 30 parts by weight of a physiologically active ingredient; and
(d) 0.001 to 49 parts by weight of water.

(2) A liquid composition containing the following components (a) to (d):
(a) 50 to 80 parts by weight of a solvent having no nitrogen atom and having a carbonyl or sulfonyl group in the molecule;
(b) 20 to 49.9 parts by weight of at least one component selected from the group consisting of a non-cyclic alcohol, an alkylene glycol, a polyalkylene glycol, a triol, a glycol monoacetate and a glycol monoalkyl ether;
(c) 0.001 to 30 parts by weight of a physiologically active ingredient; and
(d) 0.001 to 19 parts by weight of water.

(3) The liquid composition as described in (1) or (2), which further contains a dye as the component (e).

(4) The liquid composition as described in (1) or (2), which further contains 0.001 to 1 part by weight of a dye as the component (e), based on the total of the composition.

(5) The liquid composition as described in any one of (1) to (4), wherein the solvent having no nitrogen atom and having a carbonyl or sulfonyl group in the molecule is at least one selected from the group consisting of lactones, sulfoxides, cyclic ketones, and cyclic carbonate esters.

(6) The liquid composition as described in any one of (1) to (5), wherein the physiologically active ingredient is an agrochemical active ingredient.

(7) The liquid composition as described in (6), wherein the agrochemical active ingredient is a neonicotinoid insecticidal active ingredient.

(8) The liquid composition as described in (6), wherein the agrochemical active ingredient is at least one selected from the group consisting of acetamiprid, clothianidin, thiamethoxam, thiacloprid, imidacloprid, dinotefuran, and nitenpyram.

(9) The liquid composition as described in any one of (3) to (8), wherein the dye is at least one selected from the group consisting of an acidic dye, a basic dye, a mordant dye, an acid mordant dye, a direct dye, a disperse dye, a sulfur dye, a vat dye, an azoic dye, an oxidation dye, a reactive dye, an oil-soluble dye, a food colorant, a natural colorant, and a fluorescent whitening agent.

(10) The liquid composition as described in any one of (3) to (8), wherein the dye is at least one selected from the group consisting of a food colorant, a natural colorant, an Alizarine Green G, a Quinizarin Green SS, a Brilliant Green, Methylene Blue, Sun Yellow, and Sudan Yellow GG.

(11) The liquid composition as described in (9) or (10), wherein the natural colorant is at least one selected from the group consisting of a carotenoid-based colorant, a flavonoid-based colorant, a porphyrin-based colorant, a Turmeric oleoresin colorant, a monascus yellow colorant, a monascus colorant, a gardenia colorant, a beet red, sodium copper chlorophyllin, a gardenia blue colorant, a *spirulina* colorant, a plant charcoal colorant, and a caramel colorant.

According to a second aspect of the present invention, the following processes (12) to (14) for producing the liquid compositions are provided.

(12) A process for producing a liquid composition, including adding an aqueous solution containing a dye to a solvent having no nitrogen atom and having a carbonyl or sulfonyl group in the molecule, and mixing them.

(13) A process for producing the liquid composition as described in (3) or (4), including adding an aqueous solution containing a dye to the liquid composition as described in (1), and mixing them.

(14) A process for producing the liquid composition as described in (3) or (4), including adding an aqueous solution containing a dye to the liquid composition as described in (2), and mixing them.

According to a third aspect of the present invention, the ectoparasite controlling agent for use in mammals and avians as described in (15) below is provided.

(15) An ectoparasite controlling agent for use in mammals and avians, comprising the liquid composition as described in any one of (7) to (11).

Advantageous Effects of the Invention

The liquid composition of the present invention provides excellent dye stability against light and/or heat.

A uniform color development of the dye can be obtained over a long period of time by dissolving a dye that is easily decomposable by light or heat in the liquid composition of the present invention.

According to the production process of the present invention, a liquid composition having the dye uniformly dissolved can be obtained by preliminarily dissolving a dye in some water, even with the use of a dye having a low solubility in an organic solvent.

According to the present invention, a liquid composition for controlling an ectoparasite, which is highly safe for humans and animals, and shows neither phase separation of the liquid nor precipitation of effective components, can be obtained with the use of a solvent giving substantially no skin irritation.

BEST MODE FOR CARRYING OUT THE INVENTION

Figure 1:
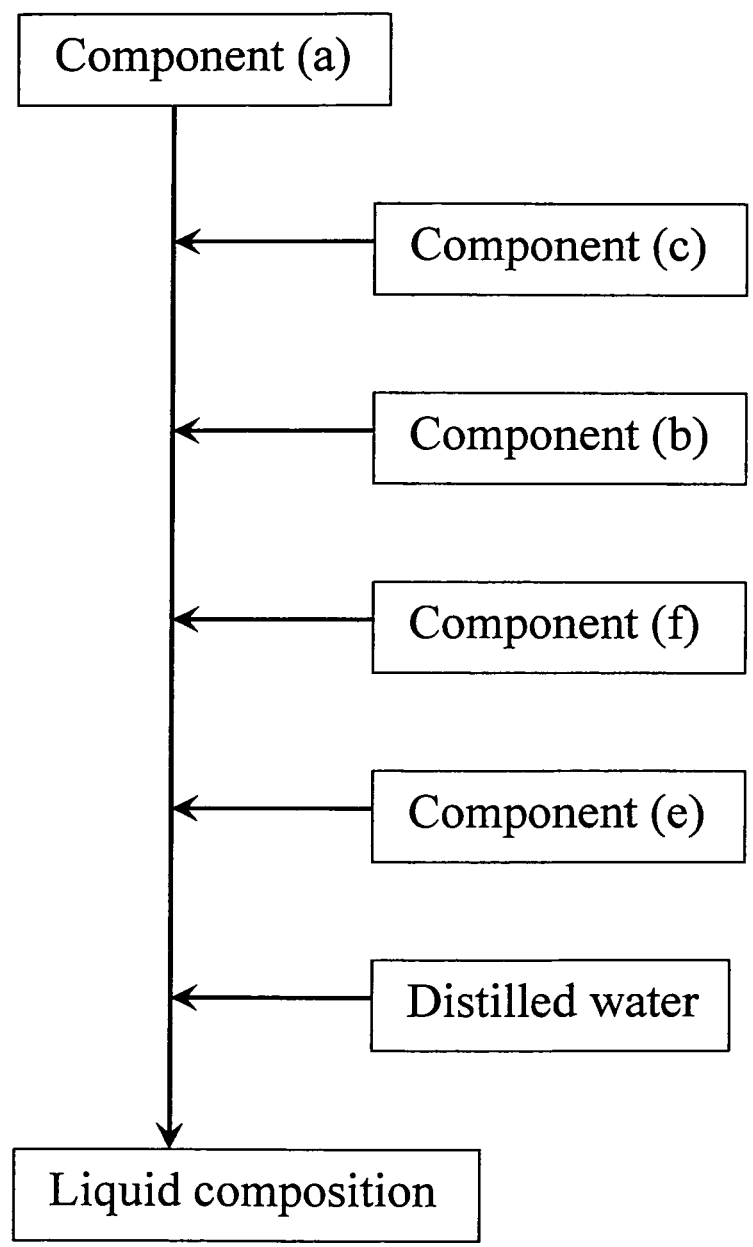
FIG. 1 is a flow chart showing a process for producing the liquid composition (C).

Hereinbelow, the present invention will be described in detail in the categories of 1) a liquid composition, 2) a process for producing the liquid composition, and 3) an ectoparasite controlling agent for use in mammals and avians.

1) Liquid Composition

The liquid composition of the present invention is any one of the following compositions (A) to (D).

Composition (A):
(a) 21 to 70 parts by weight of a solvent having no nitrogen atom and having a carbonyl or sulfonyl group in the molecule,
(b) 30 to 78.9 parts by weight of at least one component selected from the group consisting of a non-cyclic alcohol, an alkylene glycol, a polyalkylene glycol, a triol, a glycol monoacetate and a glycol monoalkyl ether,
(c) 0.001 to 30 parts by weight of a physiologically active ingredient, and
(d) 0.001 to 49 parts by weight of water.

Composition (B):
(a) 50 to 80 parts by weight of a solvent having no nitrogen atom and having a carbonyl or sulfonyl group in the molecule,
(b) 20 to 49.9 parts by weight of at least one component selected from the group consisting of a non-cyclic alcohol, an alkylene glycol, a polyalkylene glycol, a triol, a glycol monoacetate and a glycol monoalkyl ether,
(c) 0.001 to 30 parts by weight of a physiologically active ingredient, and
(d) 0.001 to 19 parts by weight of water.

Composition (C):
(a) 21 to 70 parts by weight of a solvent having no nitrogen atom and having a carbonyl or sulfonyl group in the molecule,
(b) 30 to 78.9 parts by weight of at least one component selected from the group consisting of a non-cyclic alcohol, an alkylene glycol, a polyalkylene glycol, a triol, a glycol monoacetate and a glycol monoalkyl ether,
(c) 0.001 to 30 parts by weight of a physiologically active ingredient,
(d) 0.001 to 49 parts by weight of water, and
(e) a dye.

Composition (D):
(a) 50 to 80 parts by weight of a solvent having no nitrogen atom and having a carbonyl or sulfonyl group in the molecule,
(b) 20 to 49.9 parts by weight of at least one component selected from the group consisting of a non-cyclic alcohol, an alkylene glycol, a polyalkylene glycol, a triol, a glycol monoacetate and a glycol monoalkyl ether,
(c) 0.001 to 30 parts by weight of a physiologically active ingredient,
(d) 0.001 to 19 parts by weight of water, and
(e) a dye.

(a) Solvent Having No Nitrogen Atom and Having a Carbonyl or Sulfonyl Group in the Molecule The liquid composition of the present invention contains a solvent having no nitrogen atom and having a carbonyl or sulfonyl group in the molecule (which may be hereinafter referred to as the "component (a)") as the component (a).

The solvent having no nitrogen atom and having a carbonyl or sulfonyl group in the molecule, as used in the present invention, is not particularly limited, as long as it contains no nitrogen atom in the molecule, and has a carbonyl or sulfonyl group.

Preferable specific examples thereof include at least one selected from the group consisting of lactones, sulfoxides, cyclic ketones, and cyclic carbonate esters.

The lactones are not particularly limited, but they may be any one of γ-lactone, δ-lactone, ε-lactone, macrocyclic lactone, and the like.

Specific examples of the lactone compound include β-butyrolactone, β-propiolactone, γ-butyrolactone, γ-valerolactone, δ-valerolactone, and ε-dodecalactone.

Examples of the sulfoxides include dimethyl sulfoxide, diethyl sulfoxide, methylethyl sulfoxide, dipropyl sulfoxide, diphenyl sulfoxide, and methylphenyl sulfoxide.

Examples of the cyclic ketones include cyclopentanone, methylcyclopentanone, cyclohexanone, methylcyclohexanone, cycloheptanone, 4,4-dimethoxy-2-butanone, (3,4-dimethoxyphenyl)acetone, 2-(1-cyclohexenyl)cyclohexanone, 4-hydroxy-2-butanone, isophorone, cyclooctanone, and cyclohexanonedimethylacetal.

Examples of cyclic carbonate esters include ethylene carbonate, propylene carbonate, and butylene carbonate.

The content of the component (a) is 21 to 70 parts by weight, based on 100 parts by weight of the composition (A) or composition (C), or 50 to 80 parts by weight, based on 100 parts by weight of the composition (B) or composition (D). By using the component (a) in this range, a liquid composition in which a dye is excellent in stability against light and/or heat can be obtained.

(b) At Least One Component Selected from the Group Consisting of a Non-Cyclic Alcohol, an Alkylene Glycol, a Polyalkylene Glycol, a Triol, a Glycol Monoacetate and a Glycol Monoalkyl Ether The liquid composition of the present invention may contain at least one component selected from the group consisting of a non-cyclic alcohol, an alkylene glycol, a polyalkylene glycol, a triol, a glycol monoacetate and a glycol monoalkyl ether (which may be hereinafter referred to as the "component (b)") as the component (b).

Examples of the non-cyclic alcohol as used in the present invention include aliphatic alkanols having 1 to 20 carbon atoms, which may have substituents. Examples thereof include ethyl alcohol, propyl alcohol, isopropyl alcohol, butyl alcohol, isobutyl alcohol, t-butyl alcohol, pentyl alcohol, isoamyl alcohol, hexyl alcohol, heptyl alcohol, octyl alcohol, nonyl alcohol, 2-ethyl-1-hexanol, decyl alcohol, tridecyl alcohol, 2-octyl-1-dodecanol, tetrahydrofurfuryl alcohol, 3-methoxy-1-butanol, cyclohexanol, 3-methyl-3-methoxy-1-butanol, furfuryl alcohol, 3,5-dimethyl-1-hexyn-3-ol, 2-phenoxyethanol, and glycidol.

Examples of the alkylene glycol include ethylene glycol, diethylene glycol, triethylene glycol, propylene glycol, dipropylene glycol, 3-butylene glycol, butyl diglycol, hexylene glycol, isopropylene glycol, 1,3-butanediol, 1,5-pentanediol, ethylenetriglycol, 1,4-butanediol, 2-methyl-1,5-pentanediol, 2-methyl-2,4-pentanediol, octanediol, ethylene diglycol, and butyl diglycol.

Examples of the polyalkylene glycol include polyethylene glycol, polypropylene glycol, and polybutylene glycol.

Examples of the triol include 1,2,6-hexanetriol and glycerin.

Examples of the glycol monoacetate include ethylene glycol monoacetate, diethylene glycol monoethyl ether acetate, and 3-methyl-3-methoxy-1-butylacetate.

Examples of the glycol monoalkyl ether include ethylene glycol monomethyl ether, ethylene glycol monoethyl ether, ethylene glycol isopropyl ether, ethylene glycol monobutyl ether, ethylene glycol isoamyl ether, ethylene glycol monophenyl ether, ethylene glycol benzyl ether, ethylene glycol monohexyl ether, diethylene glycol monomethyl ether, diethylene glycol monoethyl ether, diethylene glycol monobutyl ether, diethylene glycol methylethyl ether, triethylene glycol monomethyl ether, propylene glycol monomethyl ether, propylene glycol monoethyl ether, propylene glycol monobutyl ether, dipropylene glycol monomethyl ether, and dipropylene glycol monoethyl ether.

These may be used alone or in combination of two or more kinds thereof.

The content of the component (b) is 30 to 78.9 parts by weight, based on 100 parts by weight of the composition (A) or composition (C), or 20 to 49.9 parts by weight, based on 100 parts by weight of the composition (B) or composition (D). By using the component (b) in this range, a liquid composition in which a dye is excellent in stability against light and/or heat can be obtained.

(c) Physiologically Active Ingredient

The liquid composition of the present invention contains a physiologically active ingredient (which may be hereinafter referred to as "component (c)") as the component (c).

The physiologically active ingredient as used in the present invention is not particularly limited. Examples thereof include an agrochemical active ingredient, and a pharmaceutically active ingredient, and among them, preferred is the agrochemical active ingredient. The physiologically active ingredients may be used alone or in combination of two or more kinds thereof.

As the agrochemical active ingredient, a sterilizer, an insecticide, an acaricide, a plant growth regulator, a herbicide, a rodenticide, an anti-microbial agent, an anti-fungal agent, an anti-algae agent, and the like, as described below, can be exemplified.

Examples of the sterilizer include CNA, DPC, EDDP, IBP, PCNB, TPN, *agrobacterium*, isoprothiolane, ipconazole, iprodione, iminoctadine albesilate, iminoctadine acetate, imibenconazole, echlomezole, oxadixyl, oxycarboxin, oxytetracycline, oxine copper, oxolinic acid, kasugamycin, carbendazol, quinoxaline, captan, chloroneb, diethofencarb, diclomezine, dithianon, zineb, difenoconazole, cyproconazole, dimethirimol, ziram, streptomycin, sulfenic acids (dichlorfluanid), dazomet, thiadiazine, thiabendazole, thiophanate methyl, triazine, tecloftalam, tebuconazole, copper terephthalate, triadimefon, triazine, trichlamide, tricyclazole, triflumizole, triforine, tolclofos methyl, copper nonylphenol sulfonate, validamycin, bitertanol, hydroxyisoxazole, pyrazophos, pyrifenox, pyroquilon, vinclozolin, fenarimol, ferimzone, phthalide, blasticidin, fluazinam, fluoroimide, flusulfamide, flutolanil, prochloraz, procymidone, propamocarb hydrochloride, propiconazole, propineb, probenazole, hexaconazole, pefurazoate, pencycuron, benthiazole, fosetyl, polyoxin, polycarbamate, myclobutanil, mildiomycin, methasulfocarb, metalaxyl, mepanipyrim, mepronil, and probenazol copper sulfate.

Examples of the insecticide include BPMC, BPPS, BRP, CPCBS, CVMP, CVP, CYAP, DCIP, DEP, ECP, EPN, ESP, MIPC, MPMC, MPP, MTMC, PAP, PHC, PMP, XMC, acrinathrin, acetamiprid, acephate, amitraz, alanycarb, allethrin, isoxathion, isofenphos, imidacloprid, ethiofencarb, ethion, ethylthiometon, etofenprox, ethoprophos MC, etrimfos, oxamyl, sodium oleate, cartap, carbosulfan, quinalphos, clofentezine, chlorpyrifos, chlorpyrifosmethyl, chlorfluazuron, chlorobezilate, kerosene, salithion, dienochlor, cycloprothrin, cyhalothrin, cyfluthrin, diflubenzuron, cypermethrin, dimethylvinphos, dimethoate, cyromazine, sulprofos, diazinon, thiodicarb, thiometon, tetradifon, tebufenpyrad, tefluthrin, teflubenzuron, tralomethrin, nitenpyram, vamidothion, halfenprox, bifenthrin, pyraclofos, pyradaphenthion, pyridaben, pirimicarb, pynmidifen, pirimiphos methyl, fipronil, phenisobromolate, fenoxycarb, fenothiocarb, fenvalerate, fenpyroximate, fenpropathrin, buprofezin, furathiocarb, flucythrinate, prothiofos, propaphos, profenofos, hexythiazox, permethrin, bensultap, benzoxepin, benzomate, bendiocarb, benfuracarb, phosalone, fosthiazate, a polynactins composite, polybutene, formothion, malathion, mesulfenfos, methomyl, metaldehyde, monocrotophos, resmethrin, levamisole hydrochloride, fenbutatin oxide, and morantel tartrate.

Examples of the herbicide include 2,4-PA, ACN, CNP, DAP, DBN, DCBN, DCMU, DCPA, DPA, DSMA, IPC, MBPMC, MCC, MCP, MCPB, MCPP, MDBA, PAC, SAP, TCA, TCTP, ioxynil, asulam, atrazine, amiprofos methyl, ametryn, alachlor, alloxydim, isouron, isoxaben, imazapyr, imazosulfuron, esprocarb, ethidimuron, oxadiazon, orthobencarb, karbutilate, quizalofop ethyl, quinchlorac, glyphosate, chlomethoxynil, clomeprop, chlorphthalim, cyanazine, sodium cyanate, diquat, dithiopyr, siduron, cinosulfuron, diphenamid, simazine, dimethametryn, simetryn, dimepiperate, terbacil, daimuron, thiazafluoron, thifensulfuron methyl, tetrapion, thenylchlor, tebuthiuron, triclopyr, trifluralin, naproanilide, napropamide, paraquat, bialaphos, picloram, bifenox, piperophos, pyrazoxyfen, pyrazosulfuron ethyl, pyrazolate, pyributicarb, fenoxaprop ethyl, phenothiol, phenmedipham, butachlor, butamifos, flazasulfron, fluazifop, pretilachlor, prodiamine, propyzamide, bromacil, prometryn, bromobutide, hexazinone, bethrogine, bensulfuron methyl, benzofenap, bentazone, benthiocarb, pendamethalin, fosamine ammonium, methyl daimuron, metsulfuron methyl, metolachor, metribuzin, mefenacet, molinate, linuron, and lenacil.

Examples of the rodenticide include coumarins, chlorophacinone, thallium sulfate, sodium monofluoroacetate, and zinc phosphide.

Examples of the anti-microbial agent, the anti-fungal agent, and the anti-algae agent include trialkyltriamine, ethanol, isopropyl alcohol, propyl alcohol, trisnitro, chlorobutanol, pronopol, glutaraldehyde, formaldehyde, α-bromcinnamaldehyde, Skane M-8, caisson CG, NS-500 W, BIT, n-butyl BIT, allyl isothiocyanate, thiabendazole, methyl 2-benzimidazolyl carbamate, lauricidine, biovan, triclocarban, halocarban, glasisicar, benzoic acid, sorbic acid, caprylic acid, propionic acid, 10-undecylenic acid, potassium sorbate, potassium propionate, potassium benzoate, monomagnesium phthalate, zinc undecylenate, 8-hydroxyquinoline, copper quinoline, TMTD, triclosan, dichlohelanilide, tolyfluranid, milt protein, egg white lysozyme, benthiazole, sodium carbam, triazine, tebuconazole, hinokithiol, tetrachloroisophthalonitrile, tectamer 38, chlorhexidine gluconate, chlorhexidine hydrochloride, polyhexamethylene biguanide, polybiguanide hydrochloride, danthoprom, clidant, sodium pyrithion, zinc pyrithion, densil, kappa-pyrithion, thymol, isopropyl methyl phenol, OPP, phenol, butyl paraben, ethyl paraben, methyl paraben, propyl paraben, metacresol, orthocresol, paracresol, sodium orthophenyl phenol, chlorofen, parachlorophenol, parachloro methaxylate, parachlorocresol, fluorfolpet, polylysine, biopan P-1487, Jote methylparatolylsulfone, polyvinylpyrrolidone parachloroisocyanel, hydrogen peroxide, stabilized chlorine dioxide, peracetic acid, copper naphthenate, novalon AG 300, silver chloride, titanium oxide, silver, zinc-calcium phosphate, Silver Ace, silver-zinc aluminosilicate, silver-zinc zeolite, novalon AGZ330, phorone killer, Dimer 136, didecyl dimethyl ammonium chloride, Bardac 2250/80, benzotonium chloride, cetylammonium bromide, Cetrimide, CTAB, Cetavlon, Dimer 38, benzalkonium chloride, Hyamine 3500J, BARDAC 170P, DC-5700, cetylpyridinium chloride, chitosan, deuron, DCMU, prepentol A6, CMI, 2Cl-OIT, BCM, ZPT, BNP, OIT, IPBC, and TCMSP.

Examples of the plant growth regulator include abscisic acid, inabenfide, indole butyric acid, uniconazole, ethychlozate, ethephon, oxyethylene docosanol, oxine sulfate, calcium chloride, calcium sulfate, calcium peroxide, quinoxaline, DEP, cloxyfonac, chlormate, *chlorella* extracts, choline chloride, cyanamide, dichlorprop, gibberellin, daminozide, decyl alcohol, trinexapac ethyl, paclobutrazole, paraffin, piperonyl butoxide, pyraflufen ethyl, flurprimidol, prohydrojasmon, prohexadione calcium, benzylaminopurine, pendamethalin, benfuracarb, inabenfide, forchlorfenuron, potassium maleic hydrazide, mepiquat chloride, 1-naphthylacetamide, 4-CPA, MCPA thioethyl, and MCPB.

Among them, in the present invention, as the physiologically active ingredient, more preferred is a neonicotinoid agrochemical active ingredient, and particularly preferred is at least one selected from the group consisting of acetamiprid, clothianidin, thiamethoxam, thiacloprid, imidacloprid, dinotefuran, and nitenpyram.

The content of the component (c) can be suitably selected according to the kinds of the physiologically active ingredient to be used, and the applications of the liquid composition, but it is usually 0.001 to 30 parts by weight, preferably 1 to 20 parts by weight, based on 100 parts by weight of the compositions (A) to (D).

(d) Water

The liquid composition of the present invention contains water as the component (d).

As water to be used, one having a low content of impurities is preferred. For example, well water, service water, tap water, distilled water, ion-exchange water, or the like can be used.

The content of water is 0.001 to 49 parts by weight, based on 100 parts by weight of the composition (A) or composition (C), or 0.001 to 19 parts by weight, based on 100 parts by weight of the composition (B) or composition (D). Within this range, by using water as the component (d), a liquid composition in which a dye is excellent in stability against light and/or heat can be obtained.

(e) Dye

The compositions (C) and (D) contain a dye (which may be hereinafter referred to as "component (e)") as the component (e).

Among colorants, the dye to be used for the present invention refers to a substance having an affinity for materials such as fibers, capable of being dissolved in water or an organic solvent, and exhibiting a dyeing ability by being selectively absorbed from the solvent.

Furthermore, the colorant refers to a color substance that selectively absorbs visible light and develops its inherent color.

The dye that is used in the liquid composition of the present invention is not particularly limited. Examples thereof include an acidic dye, a basic dye, a mordant dye, an acid mordant dye, a direct dye, a disperse dye, a sulfur dye, a vat dye, an azoic dye, an oxidation dye, a reactive dye, an oil-soluble dye, a food colorant, a natural colorant, and a fluorescent whitening agent. Theses dyes may be used alone or in combination of two or more kinds thereof.

The acidic dye is a water-soluble dye having an acidic hydrophilic group such as a sulfonic acid group and a carboxylic group. Representative examples thereof include Acid Orange 7 (Orange II), Methyl Red and the like.

The basic dye is a dye that forms a salt with cations containing a basic group such as an amino group, a substituted amino group, and a nitrogen-containing heterocyclic group, and colorless anions. Representative examples thereof include Crystal Violet, Bismarck Brown G, Basic Blue 9 (Methylene Blue), and the like.

The mordant dye is a dye which dyes by preliminarily treating fibers with a water-soluble metal salt (mordant agent) to make a metal oxide by heat hydrolysis, and then dyeing to generate an insoluble metal complex salt compound on the fibers. Representative examples thereof include Alizarin Mordant Red 11, and the like.

The acid mordant dye is a dye having properties of both the acidic dye and the mordant dye. Representative examples thereof include Eriochrome Black T, Mordant Black 3, and the like.

The direct dye is a water-soluble dye that can dye directly cellulose fibers such as cotton and rayon. Representative examples thereof include Congo Red and Direct Red 2, and the like.

The disperse dye is a dye for dyeing hydrophobic fibers in a disperse dye-bath with a water-insoluble dye. Representative examples thereof include Disperse Red 73, Disperse Orange 3, Disperse Red 17, Disperse Violet 1, and the like.

The sulfur dye is a sulfur-containing dye that is produced by melting (vulcanizing) a relatively simple aromatic compound such as aminophenol, indolphenol, and nitrophenol, with sodium sulfide or sulfur. Representative examples thereof include Sulfur Black B, and the like.

The vat dye is a dye originally insoluble in water. With this dye, there is employed a dyeing process including making the dye water soluble (an alkali salt of a leuco compound) by reducing it in the presence of alkali followed by bringing it into contact with air for oxidation, and thereby regenerating the original dye on the fiber. Representative examples thereof include Vat Red 1, Vat Blue 1 (Indigo), and the like.

The azoic dye is different from the ready-made dyes, and intended to accomplish dyeing by reacting 2 water-soluble components (a diazo component and a coupling component) on the cellulose fibers to make it a water-insoluble azo dye. Representative examples of the grounding agent include Naphthol AS, and further, representative examples of the color developer include Fast Blue B Base.

The oxidation dye is a dye intended to accomplish a dyeing process for generating an insoluble dye by oxidation of an aromatic amine, a diamine, or aminophenols on the fibers. Representative examples thereof include Aniline Black and the like obtained by oxidation of an aniline.

The reactive dye is also referred to as a dye with reactivity, and is intended to carry out dyeing by forming covalent bonds with the fibers. Representative examples thereof include Reactive Red 24 and the like.

The oil-soluble dye is also referred to as a dye with oil-solubility, and is a dye that has no water-solubility and is soluble in many organic solvents such as mineral oils, essential oils, and fat and oils. Representative examples thereof include Solvent Red 24 and the like.

The fluorescent whitening agent exhibits fluorescence in a range of blue through violet colors, and complements the pale yellow color inherent in the fibers, thus to be seen as pure white. Representative examples thereof include Blankophor B and the like.

Among them, in the liquid composition of the present invention, at least one dyes selected from the group consisting of a food colorant, a natural colorant, Alizarine Green G Quinizarin Green SS, Brilliant Green, Methylene Blue, Sun Yellow, and Sudan Yellow GG are more preferable. These dyes are highly safe and have a low possibility of causing environmental pollution.

The food colorant is a dye that can be used as a food additive. Representative examples thereof include Food Red No. 2 (Amaranth), Food Red No. 3 (Erythrosine), Food Red No. 102 (New Coccine), Food Red No. 104 (Phloxine), Food Red No. 105 (Rose Bengal), Food Red No. 106 (Acid Red), Food Yellow No. 4 (Tartrazine), Food Yellow No. 5 (Sunset Yellow FCF), Food Green No. 3 (Fast Green FCF), Food Blue No. 1 (Brilliant Blue FCF), Food Blue No. 2 (Indigo Carmine), and Food Red No. 40 (Allura Red AC).

The natural colorant is a dye extracted from naturally occurring products, which have been traditionally used as foods. Preferable examples of the natural colorant include at least one selected from the group consisting of a carotenoid-based colorant, a flavonoid-based colorant, a porphyrin-based colorant, a Turmeric oleoresin colorant, a monascus yellow colorant, a monascus colorant, a *gardenia* colorant, beet red, sodium copper chlorophyllin, a *gardenia* blue colorant, a *spirulina* colorant, a plant charcoal colorant, and a caramel colorant.

More specific examples of these natural colorants include a carotenoid-based natural colorant such as a *gardenia* yellow colorant (crocin, crocetin), an annatto colorant (bixin, norbixin), a paprika extract colorant (capsanthin), a carrot colorant (β-carotene), a tomato colorant (lycopene), a marigold colorant (carotenoid, flavonoid), β-apo-8-carotenal, canthaxanthin, and a hot pepper colorant; a flavonoid-based natural colorant such as an onion colorant, a cyanat colorant, a pecan nut colorant, and a chicory colorant; a chalcone-based natural colorant such as a safflower yellow colorant (safflomin), and a safflower red colorant (cartamin); an anthocyanin-based natural colorant such as a *perilla* colorant (shisonin, malonylshisonin), a red cabbage colorant (cyanidin acylglycoside), a red radish colorant (pelargonidin acylglycoside), a purple sweet potato colorant (cyanidin acylglucoside, peonidin acylglucoside), a purple corn colorant, a grape fruit skin colorant (enocyanin), an elderberry colorant (cyanidin glycoside, delphinidin glycoside), a grape fruit juice colorant, a blueberry colorant, and a hibiscus colorant; a flavon-based natural colorant such as a cocoa colorant, a persimmon colorant (flavonoid), a tamarind colorant, and a kaoliang colorant (apigeninidin, luteolinidin); a flavonol-based natural colorant such as a carob colorant, and a glycyrrhiza extract colorant; a porphyrin-based natural colorant such as chlorophyll; an anthraquinone-based natural colorant such as a cotinyl colorant (carmic acid), a lac colorant (laccaic acids), and a madder colorant (alizarin, ruberythric acid);

a Turmeric oleoresin colorant (curcumin), a monascus yellow colorant (xanthomonasins), a monascus colorant (monascorubrin, ankaflavin), a *gardenia* colorant, beet red (betain-based betanin, isobetanin), sodium copper chlorophyllin, a *gardenia* blue colorant, a *spirulina* colorant (phycocyanin), a plant charcoal colorant, and a caramel colorant, and the like.

The amount of the component (e) to be blended is not particularly limited, and is suitably selected according to the applications of the liquid composition and the purposes of the incorporation of a dye, but it is preferably 0.001 to 1 part by weight, more preferably 0.005 to 0.5 parts by weight, based on 100 parts by weight of the composition (C) or (D).

(f) Other Additives

The liquid composition of the present invention may contain other additives as the component (f) if necessary, without departing from the spirit of the present invention. Examples of the other additives include a surfactant, a solvent having a nitrogen atom in the molecule, a binder, and a thickening agent.

Examples of the surfactants include a nonionic surfactant, an anionic surfactant, a cationic surfactant, and an amphoteric surfactant, and the like.

Examples of the nonionic surfactants include polyoxyalkylene nonionic surfactants such as polyoxyalkylene alkyl ethers, polyoxyalkylene alkyl phenyl ethers, polyoxyalkylene styryl phenyl ethers, polyoxyalkylene alkyl esters, polyoxyalkylene sorbitan fatty acid esters, polyoxyalkylene castor oil ethers, polyoxyethylene polyoxypropylene block polymers, and polyoxyalkylene alkylamines, but are not limited thereto. Also, the polyoxyalkylene refers to polyoxyethylene, polyoxypropylene, or a polyoxyethylene polyoxypropylene block polymer, and a mixture thereof.

Examples of the anionic surfactants include an alkali metal salt, an alkaline earth metal salt, or an ammonium salt of a higher fatty acid (C10 to 22), for example, a metal salt of a mixture of natural fatty acids obtained from a coconut oil or an animal oil, or in particular, esters of an aliphatic sulfonic acid, an aliphatic sulfuric acid, an aliphatic sulfosuccinic acid, an alkylaryl sulfonic acid, or an alkylarylsulfuric acid, and the like. The esters of the sulfonic acid, the sulfuric acid, or the sulfosuccinic acid are usually provided in the form of an alkali metal salt, an alkaline earth metal salt, an amine salt, or an ammonium salt. Further, they usually contain alkyl groups having 8 to 22 carbon atoms, and include for example, an alkyl sulfuric acid ester, a mixture of aliphatic alcohol sulfuric acid ester obtained from natural fatty acids, or sodium, potassium, calcium, or magnesium salts of a dialkyl sulfosuccinic acid ester. Examples of the alkylaryl sulfonic acid esters include dodecylbenzene sulfonic acid, naphthalene sulfonic acid, and a condensed product thereof with a formaldehyde, or a sodium, calcium, ammonium, or triethanolamine salt of a tristyrylphenol sulfuric acid ester. Examples thereof include suitable phosphates, for example, an alkylphenol containing 4 to 14 moles of ethylene oxide, and a sodium, calcium, ammonium, or triethanolamine salt of a phosphoric acid ester of a tristyrylphenol adduct Examples of the cationic surfactants include amino acid-based cationic surfactants such as an aliphatic amine, and a quaternary ammonium salt thereof, a fatty acid amide amine salt, an alkyltrialkylene glycol ammonium salt, an acylguanidine derivative, and a lower alkyl ester salt of a mono-N-long chained acyl alkali amino acid, a alkylbenzalkonium salt, an alkylpyridinium salt, and an imidazolinium salt.

These surfactants may be used alone or in combination of two or more kinds thereof.

Examples of the solvent having a nitrogen atom in the molecule include:

amide-based solvents such as N-methyl-2-pyrrolidone, formamide, N,N-dimethylformamide, and N,N-dimethylacetamide;

amine-based solvents such as 3-ethoxypropylamine, 3-methoxypropylamine, N,N-diethylethanolamine, N,N-dimethylethanolamine, n-hexylamine, N-methyl-3,3-iminobis(isopropylamine), ethanolamine, ethylamine, N-methyldiethanolamine, sec-butylamine, diethylamine, cyclohexylamine, phenethylamine, propylamine, benzylamine, n-butylamine, diisopropylamine, triethylamine, di-n-butylamine, tri-n-butylamine, dicyclohexylamine, dibenzylamine, tri-n-octylamine, dialkylamine, trialkylamine, t-butylamine, di-2-ethylhexylamine, 2-ethylhexylamine, 3-(2-ethylhexyloxy)propylamine, allylamine, isopropanolamine, N,N-dibutylethanolamine, N-(2-aminoethyl)ethanolamine, and N,N-diisopropylethylamine;

diamine-based solvents such as ethylenediamine, 1,2-diaminopropane, 1,3-diaminopropane, 1,4-diaminobutane, 3-(diethylamino)propylamine, 3-(dimethylamino)propylamine, 3-(methylamino)propylamine, 3,3-iminobis(propylamine), tetramethyl-1,3-diaminopropane, N,N,N,N,-tetramethyl-1,6-hexamethylenediamine, 3-(dibutylamino)propylamine, N-methylethanolamine, 2-hydroxyethylaminopropylamine, and tetramethylethylenediamine;

cyclic amine-based solvents such as pyridine methanol, 2-cyanopyrazine, 2-vinylpyridine, 2-methylpyrazine, 3-aldehydepyridine, N-(3-aminopropyl)morpholine, N-methylpiperazine, acryloylmorpholine, quinoline, piperazine, pyridine, pyrrolidine, 2,5-dimethylpyrazine, bisaminopropylpiperazine, quinaldine, morpholine, N-methylpiperazine, 1-amino-4-methylpiperazine, 2-chloropyridine, 2-pipecoline, 4-pipecoline, 3-pipecoline, (hydroxyethyl)piperazine, 1-(2-aminoethyl)piperazine, polyvinylpyrrolidone, and ethyleneimine;

amino acryl-based solvents such as N,N-dimethylacrylamide, acrylic acid dimethylaminoethyl ester, ethyl-3-dimethylaminoacrylate, and dimethylaminoethyl methacrylate;

nitrile-based solvents such as acrylonitrile, acetonitrile, 3,3-dimethoxypropionitrile, 3,3-imminodipropionitrile, acetone cyanhydrine, ethylene cyanhydrine, benzonitrile, and propionitrile;

hydrazine-based solvents such as dimethyl hydrazine and monomethyl hydrazine;

nitro compound-based solvents such as nitromethane, 2-nitropropane, nitrotoluene, and 1-nitropropane, nitroethane;

aniline-based solvents such as α-picoline, β-picoline, γ-picoline, aniline, N,N-diethylaniline, o-nitroanisole, toluidine, anisidine, 2-propylpyridine, 2,4,6-collidine, N,N-dimethylaniline, N-ethylaniline, xylidine, N,N-diglycidylaniline, N,N-diglycidyl o-toluidine, benzyl ethyl aniline, 2,4,6-tris(dimethylaminomethyl)phenol, m-aminobenzotrifluoride, p-phenetidine, m-xylenediamine, and mesidine; and other nitrogen-containing compound solvents such as triallylisocyanurate, o-tolidine diisocyanate, diallyl dimethyl ammonium chloride, ammonium thioglycolate, tolylene diisocyanate, hexamethylene diisocyanate, and methylethyl ketone oxime.

These solvents may be used alone or in combination of two or more kinds thereof.

Examples of the binders are not particularly limited, but include starch, dextrin, cellulose, methylcellulose, ethylcellulose, carboxymethylcellulose, hydroxyethylcellulose, hydroxypropylcellulose, carboxymethyl starch, pullulan, sodium alginate, ammonium alginate, a propylene alginate glycol ester, guar gum, locust bean gum bin, gum arabic, xanthan gum, gelatine, casein, polyvinylalcohol, polyethylene oxide, polyethylene glycol, ethylene/propylene block polymers, sodium polyacrylate, polyvinylpyrrolidone, and carrageenan.

Theses binders may be used alone or in combination of two or more kinds thereof.

Examples of the thickening agents include hydroxyalkyl cellulose, carboxymethyl cellulose, and cellulose derivatives of their metal salts or the like, polyvinylalcohol derivatives, polyvinylpyrrolidone, natural gums, and bentonite.

Furthermore, the liquid composition of the present invention may contain a solid or liquid auxiliary agent such as a stabilizer, for example, vegetable oils which may be epoxylated or not (for example, epoxylated coconut oil, rapeseed oil, or soybean oil), a defoamer (for example, silicone oil), a viscosity adjuster, a binder and/or an adhesive, and other effective components, for example, a bactericide, a fungicide, an anti-bacterial agent, or an acaricide.

The liquid composition of the present invention may be used as it is, or may also be used with various types of formulations with powders, granulates, tablets, hydrates, granular hydrates, capsules, liquids, emulsions, suspensions, emulsified suspensions, hydrated suspensions, oily suspensions, or the like, together with a suitable auxiliary agent. Further, in addition to the above-described types of the formulations, any of the formulations that are usually in use in the art are available, within the range giving no adverse effect on the purpose of the present invention.

The liquid composition of the present invention containing an agrochemical active ingredient as the component (c) is used as it is, or after being diluted with water or the like, then used on seeds, plants, water surfaces, or soil. Furthermore, it can be used in combination with other sterilizers, insecticides, herbicides, spreading agents, fertilizers, soil modifiers, or the like.

Particularly, in a case where the liquid composition of the present invention contains an insecticidally active ingredient, preferably a neonicotinoid-based, insecticidally active ingredient, as the component (c), it is useful as an ectoparasite controlling agent for use in mammals and avians, as described below.

Furthermore, the liquid composition of the present invention can be used as a soil pest controlling agent, a termite controlling agent, an agent for clothes, a pest controlling agent, a wood pest controlling agent, a bait, an ectoparasite controlling agent in animals, a hygiene pest controlling agent, a domestic pest blocking agent, an ink-jet printer ink, a dye, a ship bottom paint, an anti-algae agent for fishing nets, antimold agents for wood, or the like, in addition to the agricultural applications.

2) Process for Producing the Liquid Composition

In the liquid composition of the present invention, the compositions (A) and (B) can be obtained by mixing and uniformly dissolving the component (a), the component (b), the component (c), and water (d), and if desired, a surfactant (f) (which may be hereinafter referred to as the "component (f)"), at predetermined ratios.

The method for uniformly dissolving the component (a), the component (b), the component (c), and water (d), and if desired, the component (f) is not particularly limited. For example, methods using a stirring bath equipped with a stirrer in a bath, a jet mixer, a static mixer, or a valve homogenizer, an ultrasonic homogenizer, an extruder, may be exemplified.

The compositions (C) and (D) can be obtained, for example, by mixing and uniformly dissolving the component (a), the component (b), the component (c), and water (d), and if desired, the component (f) and the dye (e) at predetermined ratios, as shown in FIG. 1. As the method for uniformly dissolving the component (a), the component (b), the component (c), and water (d), if desired, the component (f) and the dye (e), the same methods as for formulation of the compositions (A) and (B) may be exemplified.

Figure 2:
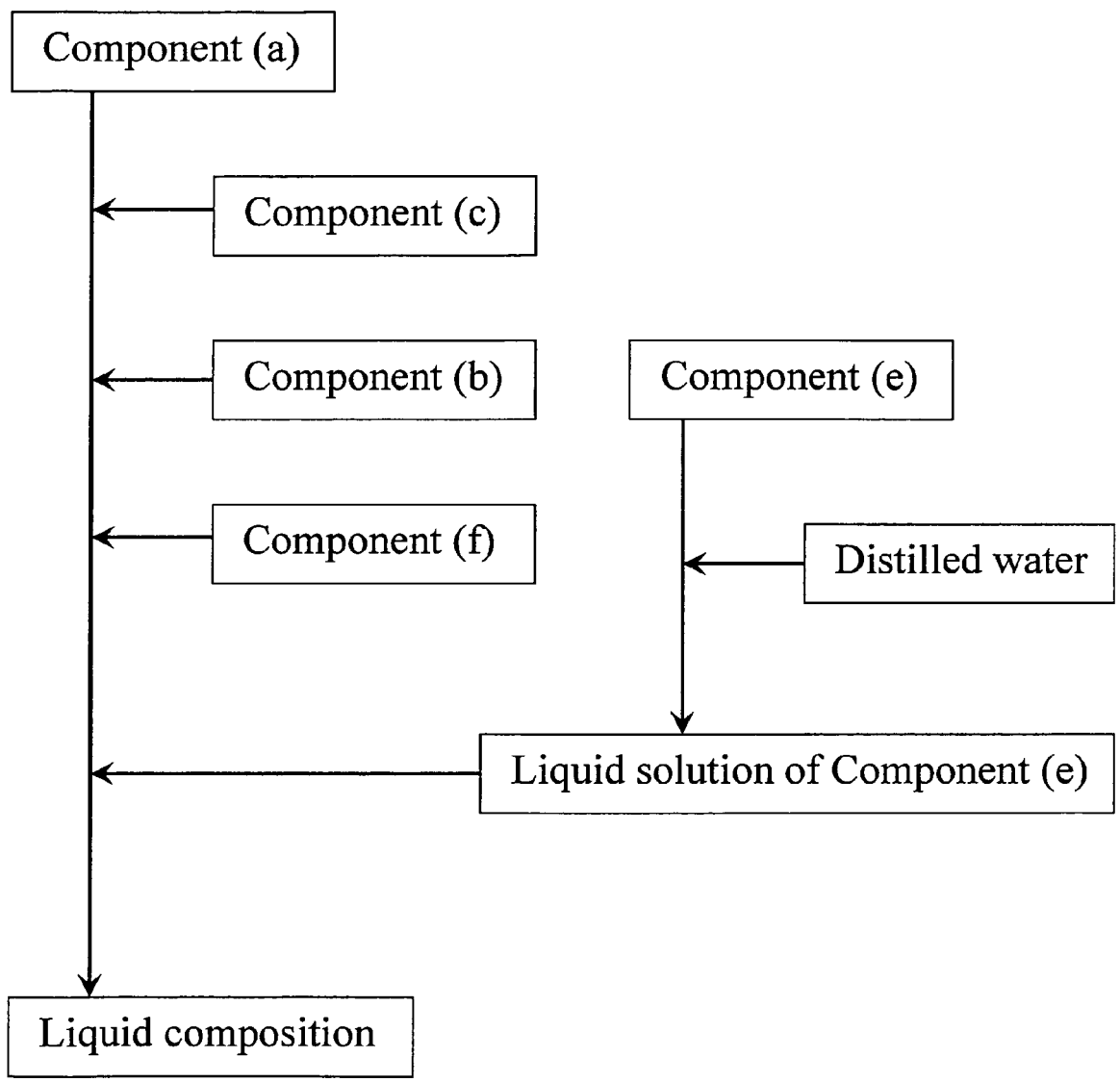
FIG. 2 is a flow chart showing another process for producing the liquid composition (C).

Furthermore, in this case, as shown in FIG. 2, in a case where the dye to be used is only slightly soluble or not soluble in an organic solvent, a liquid composition in which a dye is uniformly dissolved and develops its color can be obtained by preparing an aqueous solution of a dye preliminarily obtained by dissolving the dye in water, and adding the solution to an organic solvent. Furthermore, in the present invention, the aqueous solution of the dye may be added to the organic solvent, or the organic solvent may be added to the aqueous solution of the dye. Also, the physiologically active ingredient or any component may be added at any point of time.

3) Ectoparasite Controlling Agent for Use in Mammals and Avians

The ectoparasite controlling agent for use in mammals and avians of the present invention comprises the liquid composition of the present invention which contains an active ingredient, preferably a neonicotinoid-based, insecticidally active ingredient, as the component (c).

Examples of the mammals and avians for which the ectoparasite controlling agent for use in mammals and avians of the present invention is intended include pet animals such as dogs, cats, mice, rats, hamsters, guinea pigs, squirrels, rabbits, ferrets, and avians (such as pigeons, parrots, hill mynas, Java sparrows, true parrots, society finches, and canaries); domestic animals such as cows, horses, pigs, sheep, and goats; and poultry such as ducks, chickens, and geese.

Examples of the ectoparasite include fleas, mites, sucking lices, flies, horse flies, biting midges, and biting lices that are harmful to mammals and avians. Among them, the ectoparasite controlling agent for use in mammals and avians of the present invention is useful as a controlling agent for animal parasitic mites, or fleas.

Examples of the animal parasitic mites include ticks such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Haemaphysalis megaspinosa, Dermacentor reticulatus*, and *Dermacentortaiwanesis;* northern fowl mites such as *Dermanyssus gallinae, Ornithonyssus sylviarum*, and *Ornithonyssus bursa;* trombidioids such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi*, and *Helenicula miyagawai;* cheyletids such as *Cheyletiella yasguri, Cheyletiella parasitivorax*, and *Cheyletiella blakei;* sarcoptic mange mites such as *Psoroptes cuniculi, Chorioptes bovis, Otodectes cynotis, Sarcoptes scabiei*, and *Notoedres cati;* and demodex mites such as *Demodex canis.*

Examples of the fleas include externally parasitic wingless insects belonging to *Siphonaptera*, more specifically, fleas belonging to *Pulicidae, Ceratephyllus*, etc.

Examples of the fleas belonging to Pulicidae include *Ctenocephalides canis, Ctenocephalides felis, Pulex irritans, Echidnophaga gallinacea, Xenopsylla cheopis, Leptopsylla segnis, Nosopsyllus fascinates*, and *Monopsyllus anisus.*

Administration of the composition of the present invention to mammals and avians is carried out orally or parenterally.

Examples of the method of oral administration include methods of administering a tablet, a liquid agent, a capsule, a wafer, a biscuit, a minced meat or other feeds, and other methods.

Examples of the parenteral administration method include a method wherein the liquid composition of the present invention is formulated into a suitable formulation and then taken into the body by e.g. intravenous administration, intramuscular administration, intradermal administration, hypodermic administration, etc.; a method wherein it is administered on the body surface by spot-on treatment, pour-on treatment or spray treatment; or a method of embedding a resin fragment or the like containing the liquid composition of the present invention under the skin of the mammals and avians.

The administration dose of the liquid composition of the present invention for mammals and avians varies depending on the administration methods, the administration purposes, and the disease conditions, but it is usually at a ratio of 0.01 mg to 100 g, preferably 0.1 mg to 10 g per 1 kg of the body weight of mammals and avians.

EXAMPLES

Next, the present invention will be described in detail with reference to Examples and Comparative Examples, but the present invention is not to be limited to the following Examples in any case.

Examples 1 to 12, and Comparative Examples 1 to 12

The liquid compositions of Examples 1 to 12, and Comparative Examples 1 to 12 were prepared in a method represented by the following method B. In Examples 1 to 12 and Comparative Examples 1, 2, 4 to 12, a liquid composition in which each of the components was uniformly dissolved was obtained. However, in a case of the liquid composition of Comparative Example 3, a heterogeneous mixture in which the component (a) was not completely dissolved was obtained.

Method A: As shown in FIG. 1, by sequentially adding predetermined amounts of the component (c), the component (b), the component (f), the component (e), and (d) water to the component (a), and mixing them, a liquid composition was prepared.

Method B: As shown in FIG. 2, by sequentially adding predetermined amounts of the component (c), the component (b), and the component (f), to the component (a), and mixing them, and then adding an aqueous solution obtained by dissolving a dye as the component (e) in distilled water to the mixture, and mixing them, a liquid composition was prepared.

In the preparations of the liquid compositions of Examples 1 to 12, and Comparative Examples 1 to 12, the kinds and amounts (parts by weight) of the component (a) through the component (f) to be used, and preparation methods thereof are summarized in Table 1.

TABLE 1

|  | Component (a) (parts by weight) | Component (b) (parts by weight) | Component (c) (parts by weight) | Component (d) (parts by weight) | Component (e) (parts by weight) | Other components (parts by weight) | Preparation method |
| --- | --- | --- | --- | --- | --- | --- | --- |
| Example 1 | a-1 (32.26) | b-1 (57.66) | c-1 (8.64) | Water (0.49) | e-1 (0.01) | f-1 (0.94) | B |
| Example 2 | a-2 (32.26) | b-1 (57.66) | c-1 (8.64) | Water (0.49) | e-1 (0.01) | f-1 (0.94) | B |
| Example 3 | a-2 (30.00) | b-1 (52.01) | c-1 (7.00) | Water (10.00) | e-2 (0.05) | f-1 (0.94) | B |
| Example 4 | a-2 (40.00) | b-1 (42.01) | c-1 (7.00) | Water (10.00) | e-2 (0.05) | f-1 (0.94) | B |
| Example 5 | a-2 (50.00) | b-1 (32.01) | c-1 (7.00) | Water (10.00) | e-2 (0.05) | f-1 (0.94) | B |
| Example 6 | a-2 (60.00) | b-1 (22.01) | c-1 (7.00) | Water (10.00) | e-2 (0.05) | f-1 (0.94) | B |
| Example 7 | a-2 (70.00) | b-1 (12.01) | c-1 (7.00) | Water (10.00) | e-2 (0.05) | f-1 (0.94) | B |
| Example 8 | a-2 (30.00) | b-1 (42.01) | c-1 (7.00) | Water (20.00) | e-2 (0.05) | f-1 (0.94) | B |
| Example 9 | a-2 (40.00) | b-1 (32.01) | c-1 (7.00) | Water (20.00) | e-2 (0.05) | f-1 (0.94) | B |
| Example 10 | a-2 (50.00) | b-1 (22.01) | c-1 (7.00) | Water (20.00) | e-2 (0.05) | f-1 (0.94) | B |
| Example 11 | a-2 (30.00) | b-1 (32.01) | c-1 (7.00) | Water (30.00) | e-2 (0.05) | f-1 (0.94) | B |
| Example 12 | a-2 (21.00) | b-1 (39.51) | c-1 (8.50) | Water (30.00) | e-2 (0.05) | f-1 (0.94) | B |
| Comparative Example 1 | — | b-1 (57.66) | c-1 (8.64) | Water (0.49) | e-1 (0.01) | f-1 (0.94) NMP (32.26) | B |
| Comparative Example 2 | a-2 (80.00) | b-1 (2.01) | c-1 (7.00) | Water (10.00) | e-2 (0.05) | f-1 (0.94) | B |
| Comparative Example 3 | — | b-1 (82.01) | c-1 (7.00) | Water (10.00) | e-2 (0.05) | f-1 (0.94) | B |
| Comparative Example 4 | a-2 (10.00) | b-1 (67.01) | c-1 (7.00) | Water (40.00) | e-2 (0.05) | f-1 (0.94) | B |
| Comparative Example 5 | a-2 (20.00) | b-1 (52.01) | c-1 (7.00) | Water (20.00) | e-2 (0.05) | f-1 (0.94) | B |
| Comparative Example 6 | a-2 (20.00) | b-1 (42.01) | c-1 (7.00) | Water (30.00) | e-2 (0.05) | f-1 (0.94) | B |
| Comparative Example 7 | a-2 (20.00) | b-1 (32.01) | c-1 (7.00) | Water (40.00) | e-2 (0.05) | f-1 (0.94) | B |
| Comparative Example 8 | a-2 (30.00) | b-1 (22.01) | c-1 (7.00) | Water (40.00) | e-2 (0.05) | f-1 (0.94) | B |

TABLE 1-continued

|  | Component (a) (parts by weight) | Component (b) (parts by weight) | Component (c) (parts by weight) | Component (d) (parts by weight) | Component (e) (parts by weight) | Other components (parts by weight) | Preparation method |
|---|---|---|---|---|---|---|---|
| Comparative Example 9 | a-2 (20.00) | b-1 (22.01) | c-1 (7.00) | Water (50.00) | e-2 (0.05) | f-1 (0.94) | B |
| Comparative Example 10 | a-2 (20.00) | b-1 (62.01) | c-1 (7.00) | Water (10.00) | e-2 (0.05) | f-1 (0.94) | B |
| Comparative Example 11 | a-2 (60.00) | b-1 (12.01) | c-1 (7.00) | Water (20.00) | e-2 (0.05) | f-1 (0.94) | B |
| Comparative Example 12 | a-2 (40.00) | b-1 (22.01) | c-1 (7.00) | Water (30.00) | e-2 (0.05) | f-1 (0.94) | B |

In Table 1, as the component (a) through the component (e), the following ones were used.
(a) Solvent having no nitrogen atom and having a carbonyl or sulfonyl group in the molecule:
a-1: γ-Butyrolactone,
a-2: Propylene carbonate;
(b) At least one component selected from the group consisting of a non-cyclic alcohol, an alkylene glycol, a polyalkylene glycol, a triol, a glycol monoacetate and a glycol monoalkyl ether:
b-1: Dipropylene glycol;
(c) Physiologically active ingredient:
c-1: Acetamiprid (manufactured by Nippon Soda Co., Ltd.);
(d) Water: Distilled water;
(e) Dye:
e-1: Mixed colorant obtained by mixing 78% of Food Yellow No. 4, 2% of Food Blue No. 1, and 20% of Food Red No. 40,
e-2: Food Blue No. 1;
(f) Other components:
f-1: Pluronic PE6400 (manufactured by BASF)
NMP: N-Methyl-2-pyrrolidone Experimental Example 1

Test on Stability Against Light and Heat

The liquid compositions of Example 2 and Comparative Example 1 were put into a mono-layered polyethylene bottle having high light transmittance state, and kept in a dark room at room temperature, and a dark room at a high temperature of 54° C. for 2 weeks. On the other hand, the liquid compositions of Example 2 and Comparative Example 1 were put into a mono-layered bottle having high light transmission, made of polyethylene, and exposed to solar light. After 12 days or 2 weeks of solar light exposure, the color of the liquid preparation was evaluated in accordance with a Munsell color system by visual examination. The evaluation results are shown in Table 2.

TABLE 2

|  |  | Example 2 | Comparative Example 1 |
|---|---|---|---|
| Acetamiprid |  | 8.64 | 8.64 |
| Propylene carbonate |  | 32.26 |  |
| N-Methyl-2-pyrrolidone |  |  | 32.26 |
| Dipropylene glycol |  | 57.66 | 57.66 |
| PLURONIC L64 (PO-EO block polymers) |  | 0.94 | 0.94 |
| Blue No. 1 |  | 0.0002 | 0.0002 |
| Yellow No. 4 |  | 0.0078 | 0.0078 |
| Red No. 40 |  | 0.0020 | 0.0020 |
| Distilled water |  | 0.49 | 0.49 |
| Total |  | 100 | 100 |
| Color of preparation (as observed with visual examination) (JIS Standard color system) | Immediately after preparation | 2.5YR 5/12 | 2.5YR 5/12 |
|  | In a dark place for 2 weeks | 2.5YR 5/12 | 2.5YR 5/12 |
|  | In a dark place at 54° C. for 2 weeks | 2.5YR 6/14 | 10Y 7/10 |
|  | In a bright place for 12 days | 2.5YR 6/14 | 7.5Y 8/12 |

As shown in Table 2, the liquid composition of Example 2 was remarkably excellent in heat stability (in a case where it was kept in a dark room at 54° C. for 2 weeks) and light stability (in a case where it was exposed to light for 12 days), as compared with the liquid composition of Comparative Example 1 in which 32.26 parts by weight of N-methylpyrrolidone was used instead of 32.26 parts by weight of propylene carbonate.

Experimental Example 2

Test on Stability of the Formulation (Cooling Test)

After cooling the liquid compositions of Examples 3 to 12 and Comparative Examples 2 to 12 at −5° C., the presence or absence of separation and precipitation of the active ingredient was observed. A case where phase separation did not occur was evaluated as ○, and a case where phase separation occurred was evaluated as x. In addition, after a small amount of a piece of active ingredient crystal was added, the presence or absence of the crystal growth of the active ingredient was investigated. As a result of visual examination, a case where crystal growth was absent was considered as ⊚; a case where little crystal growth was perceived, but the solution became a uniform solution again when the temperature was returned to room temperature was considered as ○, a case where crystal growth was perceived, but the solution became a substantially uniform solution when the temperature was returned to room temperature was considered as Δ; and a case where crystal growth was perceived, and the solution did not become a uniform solution even when the temperature was returned to room temperature was considered as x. The evaluation results are shown in Table 3.

TABLE 3

|  | Cooling test | |
|---|---|---|
|  | At −5° C. for 3 days | At 24 hours after addition of a piece of active ingredient crystal |
| Example 3 | ○ | ⊚ |
| Example 4 | ○ | ⊚ |
| Example 5 | ○ | ⊚ |
| Example 6 | ○ | ⊚ |

TABLE 3-continued

| | Cooling test | |
|---|---|---|
| | At −5° C. for 3 days | At 24 hours after addition of a piece of active ingredient crystal |
| Example 7 | ○ | ◎ |
| Example 8 | ○ | ○ |
| Example 9 | ○ | ◎ |
| Example 10 | ○ | ◎ |
| Example 11 | ○ | ○ |
| Example 12 | ○ | ○ |
| Comparative Example 2 | X | ◎ |
| Comparative Example 3 | Not dissolved | Stopped |
| Comparative Example 4 | ○ | Δ |
| Comparative Example 5 | ○ | Δ |
| Comparative Example 6 | ○ | Δ |
| Comparative Example 7 | ○ | X |
| Comparative Example 8 | X | Δ |
| Comparative Example 9 | X | X |
| Comparative Example 10 | ○ | Δ |
| Comparative Example 11 | X | ○ |
| Comparative Example 12 | X | ○ |

As shown in Table 3, the liquid compositions of Examples 3 to 7, 9, and 10 had no phase separation even when they were cooled to −5° C., and had no crystal growth of an active ingredient if a piece of active ingredient crystal was added.

The liquid compositions of Examples 8, 11, and 12 had no phase separation even when they were cooled to −5° C., and had little crystal growth perceived if a piece of active ingredient crystal was added, but they became uniform solutions by returning the temperature to room temperature.

The liquid compositions of Comparative Examples 4 to 7, and 10 had no phase separation when they were cooled to −5° C., but had crystal growth perceived if a piece of active ingredient crystal was added. The liquid compositions of Comparative Examples 7 and 9 did not become uniform solutions even by returning the temperature to room temperature.

The liquid compositions of Comparative Examples 2, 8, 9, 11, and 12 had phase separation, when they were cooled to −5° C.

Experimental Example 3

Test of Dye Dissolution (Comparative Experiment 1)

By Method A, we tried to prepare a liquid composition having the same constitution as for the liquid composition prepared in Example 1. That is, a non-uniform solution was obtained by adding 0.94 parts by weight of Pluronic PE6400 (manufactured by BASF), 8.64 parts by weight of acetamiprid, 0.0078 parts by weight of Food Yellow No. 4, 0.0002 parts by weight of Food Blue No. 1, and 0.002 parts by weight of Food Red No. 40 to 32.26 parts by weight of γ-butyrolactone and 57.66 parts of dipropylene glycol. In order to dissolve the insoluble dye, 0.49 parts by weight of distilled water was added thereto, and mixed by means of a Three-One Motor, but the uniformity was not improved, and the non-uniform solution remained as it was.

The dissolution state and colors of the dye in the liquid composition obtained in Example 1, and the liquid composition obtained in Comparative Experiment 1 were observed by visual examination. The results are shown in Table 4.

TABLE 4

| | Example 1 | Comparative Experiment 1 |
|---|---|---|
| (a) γ-Butyrolactone | 32.26 | 32.26 |
| (b) Dipropylene glycol | 57.66 | 57.66 |
| (c) Acetamiprid | 8.64 | 8.64 |
| (d) Distilled water | 0.49 | 0.49 |
| (e) Dye | | |
| Food Yellow No. 4 | 0.0078 | 0.0078 |
| Food Blue No. 1 | 0.0002 | 0.0002 |
| Food Red No. No. 40 | 0.0020 | 0.0020 |
| Color of formulation (as observed with visual examination) | Brown | Red-violet |
| Solubility of colorant | Uniform Dissolution | Not dissolved |

As shown in Table 4, it was found that even for the liquid compositions having the same formulation, if the component (c), the component (b), the component (f), and the component (e) were sequentially added to the component (a), a non-uniform liquid composition was obtained, while if an aqueous solution obtained by preliminarily dissolving the component (e) in distilled water was added to a mixed solution of the component (a), the component (c), the component (b), and the component (f), and mixed, a uniform liquid composition was obtained.

Experimental Example 4

Test on Efficacy Using a Dog Against Fleas (1) Preparation of Liquid Composition

Example 13

By adding 0.94 parts by weight of a surfactant (Pluronic PE6400, manufactured by BASF), and 0.49 parts by weight of water to a solution obtained by dissolving 8.64 parts by weight of acetamiprid to a mixed solvent of 32.26 parts of γ-butyrolactone and 57.66 parts by weight of dipropylene glycol, and mixing and dissolving them by means of a Three-One Motor, a uniform solution (liquid composition) was obtained.

Comparative Example 13

By adding 1.03 parts by weight of a surfactant (Pluronic PE6400, manufactured by BASF), and 0.54 parts by weight of water to a mixed solvent of 35.31 parts by weight of γ-butyrolactone and 63.12 parts by weight of dipropylene glycol, and mixing and dissolving them by means of a Three-One Motor, a uniform solution (liquid composition) was obtained.

(2) Test on Efficacy

Predetermined liquid preparations were spot-on administered to six dogs having various body weights, and a day before the test days (2, 9, 16, 23, and 30 days after administration), predetermined numbers of fleas (*Ctenocephalidis felis*) were innoculated to the six dogs.

After a predetermined number of days had passed after administration (treatment), the numbers of parasitic fleas on the dogs were investigated, and the mortality rates were determined on the basis of the following equation.

$$\text{Mortality rate}(\%) = \{(X-Y)/X\} \times 100$$

wherein X represents the numbers of parasitic fleas on the dogs that had been treated with the liquid composition of Comparative Example 13, and Y represents the numbers of parasitic fleas on the dogs that had been treated with the liquid composition of Example 13. The results are shown in Table 5.

TABLE 5

| Sample | Amount for treatment | | Days after treatment (days) | |
|---|---|---|---|---|
| | | | 2 | 9 |
| Example 13 | 1 mL | Average value of the numbers of the remaining fleas (heads) | 3.2 | 0.7 |
| | | Mortality rate (%) | 93 | 99 |
| | 2 mL | Average value of the numbers of the remaining fleas (heads) | 2.7 | 1 |
| | | Mortality rate (%) | 94 | 98 |
| | 3 mL | Average value of the numbers of the remaining fleas (heads) | 0 | 0 |
| | | Mortality rate (%) | 100 | 100 |
| Comparative Example 13 | 3 mL | Average value of the numbers of the remaining fleas (heads) | 44.5 | 60.7 |

From Table 5, it was found that the ectoparasite-controlling liquid composition of Example 13 has an excellent flea-controlling effect.

INDUSTRIAL APPLICABILITY

The liquid composition of the present invention provides excellent dye stability against light and/or heat.

A uniform color development of the dye can be accomplished over a long period of time by dissolving a dye that is easily decomposable by light or heat in the liquid composition of the present invention.

According to the production process of the present invention, a liquid composition having a dye uniformly dissolved therein can be obtained by preliminarily dissolving the dye in some water, even with the use of dye having a low solubility in an organic solvent.

According to the present invention, an ectoparasite-controlling liquid composition, which is highly safe for humans and animals, and has neither phase separation of the liquid nor precipitation of effective components, can be obtained with the use of a solvent giving substantially no skin irritation.

The invention claimed is:

1. A liquid composition comprising the following components (a) to (d):
   (a) 21 to 50 parts by weight of a solvent, based on 100 parts by weight of the liquid composition;
   (b) 30 to 57.66 parts by weight of an alkylene glycol, based on 100 parts by weight of the liquid composition;
   (c) 7 to 8.64 parts by weight of acetamiprid, based on 100 parts by weight of the liquid composition; and
   (d) 0.49 to 30 parts by weight of water, based on 100 parts by weight of the liquid composition,
   wherein a total amount of the components which comprise the liquid composition is 100 parts by weight,
   wherein the solvent is at least one selected from the group consisting of γ-butyrolactone and propylene carbonate, and
   wherein the alkylene glycol is at least one selected from the group consisting of ethylene glycol, diethylene glycol, propylene glycol and dipropylene glycol.

2. A liquid composition comprising the following components (a) to (d):
   (a) 50 to 60 parts by weight of a solvent, based on 100 parts by weight of the liquid composition;
   (b) 20 to 32.01 parts by weight of an alkylene glycol, based on 100 parts by weight of the liquid composition;
   (c) 7 to 8.64 parts by weight of acetamiprid, based on 100 parts by weight of the liquid composition; and
   (d) 0.49 to 20 parts by weight of water, based on 100 parts by weight of the liquid composition,
   wherein a total amount of the components which comprise the liquid composition is 100 parts by weight,
   wherein the solvent is at least one selected from the group consisting of γ-butyrolactone and propylene carbonate, and
   wherein the alkylene glycol is at least one selected from the group consisting of ethylene glycol, diethylene glycol, propylene glycol and dipropylene glycol.

3. The liquid composition according to claim 1 or 2, further comprising component (e) a dye.

4. The liquid composition according to claim 3, wherein the dye is present in 0.01 to 1 parts by weight, based on 100 parts by weight of the liquid composition.

5. The liquid composition according to claim 3, wherein the dye is at least one selected from the group consisting of an acidic dye, a basic dye, a mordant dye, an acid mordant dye, a direct dye, a disperse dye, a sulfur dye, a vat dye, an azoic dye, an oxidation dye, a reactive dye, an oil-soluble dye, a food colorant, a natural colorant, and a fluorescent whitening agent.

6. The liquid composition according to claim 3, wherein the dye is at least one selected from the group consisting of a food colorant, a natural colorant, an Alizarine Green G, a Quinizarin Green SS, a Brilliant Green, Methylene Blue, Sun Yellow, and Sudan Yellow GG.

7. The liquid composition according to claim 5, wherein the natural colorant is at least one selected from the group consisting of a carotenoid-based colorant, a flavonoid-based colorant, a porphyrin-based colorant, a Turmeric oleoresin colorant, a monascus yellow colorant, a monascus colorant, a *gardenia* colorant, a beet red, sodium copper chlorophyllin, a *gardenia* blue colorant, a *spirulina* colorant, a plant charcoal colorant, and a caramel colorant.

8. A process for producing a liquid composition having components (a) to (d), and component (e) a dye, said process comprising forming a liquid mixture by mixing:
   (a) 21 to 50 parts by weight of a solvent, based on 100 parts by weight of the liquid composition;
   (b) 30 to 57.66 parts by weight of an alkylene glycol, based on 100 parts by weight of the liquid composition;
   (c) 7 to 8.64 parts by weight of acetamiprid, based on 100 parts by weight of the liquid composition; and
   (d) 0.49 to 30 parts by weight of water, based on 100 parts by weight of the liquid composition; and
   mixing the liquid mixture with an aqueous solution containing (e) a dye to obtain the liquid composition,
   wherein a total amount of the components which comprise the liquid composition is 100 parts by weight,
   wherein the solvent is at least one selected from the group consisting of γ-butyrolactone and propylene carbonate, and
   wherein the alkylene glycol is at least one selected from the group consisting of ethylene glycol, diethylene glycol, propylene glycol and dipropylene glycol.

9. An ectoparasite controlling agent for use in mammals and avians comprising the liquid composition of claim 1.

10. A process for producing a liquid composition having components (a) to (d) and component (e) 0.01 to 1 part by weight of a dye based on 100 parts by weight of the liquid composition, said process comprising:
forming a liquid mixture by mixing:
(a) 21 to 50 parts by weight of a solvent, based on 100 parts by weight of the liquid composition;
(b) 30 to 57.66 parts by weight of an alkylene glycol, based on 100 parts by weight of the liquid composition;
(c) 7 to 8.64 parts by weight of acetamiprid, based on 100 parts by weight of the liquid composition; and
(d) 0.49 to 30 parts by weight of water, based on 100 parts by weight of the liquid composition; and
mixing the liquid mixture with an aqueous solution containing the dye to obtain the liquid composition,
wherein a total amount of the components which comprise the liquid composition is 100 parts by weight,
wherein the solvent is at least one selected from the group consisting of γ-butyrolactone and propylene carbonate, and
wherein the alkylene glycol is at least one selected from the group consisting of ethylene glycol, diethylene glycol, propylene glycol and dipropylene glycol.

11. A process for producing a liquid composition having components (a) to (d), and component (e) a dye, comprising:
forming a liquid mixture by mixing:
(a) 50 to 60 parts by weight of a solvent, based on 100 parts by weight of the liquid composition;
(b) 20 to 32.01 parts by weight of an alkylene glycol, based on 100 parts by weight of the liquid composition;
(c) 7 to 8.64 parts by weight of acetamiprid, based on 100 parts by weight of the liquid composition; and
(d) 0.49 to 20 parts by weight of water, based on 100 parts by weight of the liquid composition; and
mixing the liquid mixture with an aqueous solution containing (e) the dye to obtain the liquid composition,
wherein a total amount of the components which comprise the liquid composition is 100 parts by weight,
wherein the solvent is at least one selected from the group consisting of γ-butyrolactone and propylene carbonate, and
wherein the alkylene glycol is at least one selected from the group consisting of ethylene glycol, diethylene glycol, propylene glycol and dipropylene glycol.

12. A process for producing a liquid composition having components (a) to (d), and component (e) 0.01 to 1 part by weight of a dye based on 100 parts by weight of the liquid composition comprising:
forming a liquid mixture by mixing:
(a) 50 to 60 parts by weight of a solvent, based on 100 parts by weight of the liquid composition;
(b) 20 to 32.01 parts by weight of an alkylene glycol, based on 100 parts by weight of the liquid composition;
(c) 7 to 8.64 parts by weight of acetamiprid, based on 100 parts by weight of the liquid composition; and
(d) 0.49 to 20 parts by weight of water, based on 100 parts by weight of the liquid composition; and
mixing the liquid mixture with an aqueous solution containing (e) the dye to obtain the liquid composition,
wherein a total amount of the components which comprise the liquid composition is 100 parts by weight,
wherein the solvent is at least one selected from the group consisting of γ-butyrolactone and propylene carbonate, and
wherein the alkylene glycol is at least one selected from the group consisting of ethylene glycol, diethylene glycol, propylene glycol and dipropylene glycol.

13. The liquid composition according to claim 1 or 2, wherein component (d) is from 0.49 to 19 parts by weight of water.

14. The process for producing a liquid composition according to any one of claims 8, 10, 11 and 12, wherein component (d) is from 0.49 to 19 parts by weight of water, based on 100 parts by weight of the liquid composition.

* * * * *